(12) United States Patent
Wang et al.

(10) Patent No.: US 8,252,928 B2
(45) Date of Patent: Aug. 28, 2012

(54) PROCESSES FOR THE SYNTHESIS OF FIVE AND SIX MEMBERED HETEROCYCLIC RINGS

(75) Inventors: Peter X. Wang, Clarkson Valley, MO (US); Tao Jiang, St. Louis, MO (US); David W. Berberich, St. Peters, MO (US)

(73) Assignee: Mallinckrodt LLC., Hazelwood, MO (US)

( * ) Notice: Subject to any disclaimer, the term of this patent is extended or adjusted under 35 U.S.C. 154(b) by 438 days.

(21) Appl. No.: 12/558,646

(22) Filed: Sep. 14, 2009

(65) Prior Publication Data

US 2010/0069639 A1    Mar. 18, 2010

Related U.S. Application Data

(60) Provisional application No. 61/097,236, filed on Sep. 16, 2008.

(51) Int. Cl.
*C07D 489/02* (2006.01)
*C07D 489/08* (2006.01)

(52) U.S. Cl. .......................................... 546/45; 546/44

(58) Field of Classification Search .................... 546/45, 546/44
See application file for complete search history.

(56) References Cited

FOREIGN PATENT DOCUMENTS

GB         2 392 670 A    3/2004
WO    WO 2009/078987 A1   6/2009

OTHER PUBLICATIONS

Kondo et al., "Ueber das 7-amino-dihydro-thebainon", Chemische Berichte, vol. 65, 1932, pp. 1214-1217, XP 002559782.
Brossi et al., "Structure determination of brominated morphinan-6-ones by 13CNMR . . . " Helvetica Chimica Acta, 46(5), 1981, pp. 1672-1681, XP 002559783.
Leisch et al., "Studies on regioselective hydrogenation of Thebaine and its conversion to Hydrocodone", Tetrahedron Letters, 48(23), 2007, pp. 3979-3981, XP 022069428.
Iijima et al., "studies in the (+)-morphinan series 5 . . . " J. Med. Chem.., 1978, 21(4); pp. 378-400.
Iijima et al., "studies in the (+)-morphinan series 4 . . . " J. Org. Chem.., 1978, 43(7); pp. 1462-1463.

*Primary Examiner* — Charanjit Aulakh

(57) ABSTRACT

The present invention provides processes for the synthesis of five and six membered rings. In particular, the present invention provides processes for the synthesis of five and six membered rings in alkaloids.

12 Claims, No Drawings

PROCESSES FOR THE SYNTHESIS OF FIVE AND SIX MEMBERED HETEROCYCLIC RINGS

FIELD OF THE INVENTION

The present invention generally relates to processes for the synthesis of five and six membered rings. In particular, the present invention relates to processes for the synthesis of five and six membered rings in alkaloids.

BACKGROUND OF THE INVENTION

"(−)-Nal" morphinan compounds, such as naltrexone, naloxone, nalmefene, and nalbuphine, are used in therapeutic applications as analgesics and antagonists. Recently, the (+)-nal morphinan enantiomers have been shown to have important bioactivities that differ from their (−) counterparts.

An important intermediate compound to produce a class of important (+)-opiates is (+)-dihydrothebaine. In particular, (+)-dihydrothebaine is an intermediate compound to make (+)-thebaine, which is a common intermediate to make a series of biologically active (+)-opiates, such as (+)-oxycodone, (+)-oxymorphone, (+)-naltrexone, (+)-naloxone, and (+)-nalbuphine. Traditionally, the synthesis of (+)-dihydrothebaine has required two steps: (1) synthesis of (+)-hydrocodone from dihydrosinomenine is prepared in a strong acid, and is then isolated and purified; and (2) pure (+)-hydrocodone is then converted to (+)-dihydrothebaine. This process, however, is time consuming because it requires the isolation of (+)-hydrocodone prior to its conversion to (+)-dihydrothebaine. Improved processes for the production of (+)-dihydrothebaine, and other intermediates used in the production of (+)-opiates are needed.

SUMMARY OF THE INVENTION

The present invention provides a synthetic route for the preparation of a five or six-membered heterocyclic ring in a one-pot process via an intermolecular reaction using an alcohol and a proton donor. The synthetic route may be utilized to produce a variety of compounds, including intermediate compounds used in the production of (+)-opiates.

Briefly, therefore, in one aspect the present invention encompasses a process for the preparation of a compound comprising Formula (II):

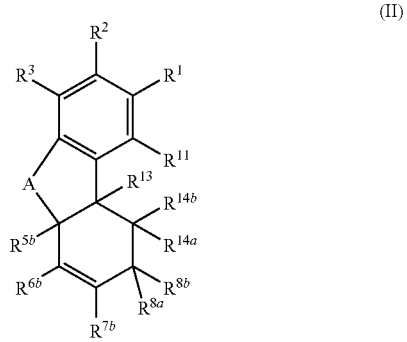

(II)

The process comprises contacting a compound of Formula (I), with an alcohol and a proton donor to form a reaction mixture. The compound of Formula (I) comprises:

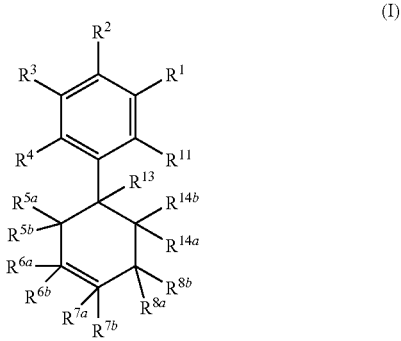

(I)

The reaction mixture is heated for a period of time sufficient to allow for the formation of the compound comprising Formula (II). For each of the compounds having Formula (I) and (II), the variables stand for the following:

A is a member of a five-membered or a six-membered heterocyclic ring;

$R^1$, $R^2$, $R^3$, and $R^{11}$ are each independently selected from the group consisting of hydrogen, hydrocarbyl, substituted hydrocarbyl, halogen, {—}OH, {—}NH$_2$, {—}SH, {—}SR$^{111}$, {—}OR$^{111}$, and {—}N(R$^{111}$)$_2$;

$R^4$ is selected from the group consisting of {—}OH, {—}SH, {—}NH$_2$, {—}NHR$^{112}$, {—}N(OH)R$^{112}$, {—}P(OH)$_2$, {—}P(OH)R$^{112}$, {—}B(OH)$_2$, {—}B(OH)R$^{112}$, and {—}Si(OH)(R$^{112}$)$_2$;

$R^{5a}$, $R^{5b}$, $R^{6a}$, $R^{6b}$, $R^{7a}$, $R^{7b}$, $R^{8a}$, $R^{8b}$, $R^{13}$, $R^{14a}$, and $R^{14b}$ are each independently selected from the group consisting of hydrogen, hydrocarbyl, substituted hydrocarbyl, halogen, ({—}OH, {—}NH$_2$, {—}SH, {—}SR$^{111}$, {—}OR$^{111}$, and {—}N(R$^{111}$)$_2$, provided that any of R$^{5a}$ and R$^{5b}$, R$^{6a}$ and R$^{6b}$, R$^{7a}$ and R$^{7b}$, R$^{8a}$ and R$^{8b}$, R$^{14a}$ and R$^{14b}$, may together form a moiety selected from the group consisting of {═}O, {═}S, and {═}NR$^{111}$;

$R^{111}$ is selected from the group consisting of hydrocarbyl and substituted hydrocarbyl;

$R^{112}$ is selected from the group consisting of {—}OH, hydrocarbyl, and substituted hydrocarbyl;

two or more R groups selected from the group consisting of $R^1$, $R^2$, $R^3$, $R^{5a}$, $R^{5b}$, $R^{6a}$, $R^{6b}$, $R^{7a}$, $R^{7b}$, $R^{8a}$, $R^{8b}$, $R^{11}$, $R^{13}$, $R^{14a}$, and $R^{14b}$ may form part of a ring or a ring system selected from the group consisting of carbocyclic rings, heterocyclic rings, aryl rings, heteroaryl rings, and combinations thereof; and two adjacent carbons attached to R groups selected from the group consisting of $R^{5a}$, $R^{5b}$, $R^{6a}$, $R^{6b}$, $R^{7a}$, $R^{7b}$, $R^{8a}$, $R^{8b}$, $R^{13}$, $R^{14a}$, and $R^{14b}$ may optionally form a carbon-carbon double bond.

Yet another aspect of the invention provides a process for the preparation of a compound comprising Formula (IIa):

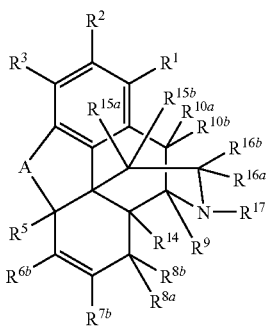

(IIa)

The process comprises contacting a compound of Formula (Ia), with an alcohol and a proton donor to form a reaction mixture. The compound of Formula (Ia) comprises:

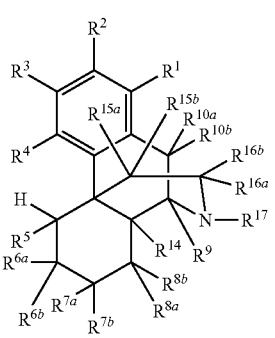

(Ia)

The reaction mixture is heated for a period of time sufficient to allow for the formation of the compound comprising Formula (IIa). For each of the compounds having Formula (Ia) and (IIa), the variables stand for the following:

A is a member of a five-membered or a six-membered heterocyclic ring;

$R^1$, $R^2$, and $R^3$ are each independently selected from the group consisting of hydrogen, hydrocarbyl, substituted hydrocarbyl, halogen, {—}OH, {—}$NH_2$, {—}SH, {—}$SR^{111}$, {—}$OR^{111}$, and {—}$N(R^{111})_2$;

$R^4$ is selected from the group consisting of {—}OH, {—}SH, {—}$NH_2$, {—}$NHR^{112}$, {—}$N(OH)R^{112}$, {—}$P(OH)_2$, {—}$P(OH)R^{112}$, {—}$B(OH)_2$, {—}$B(OH)R^{112}$, and {—}$Si(OH)(R^{112})_2$;

$R^5$, $R^{6a}$, $R^{6b}$, $R^{7a}$, $R^{7b}$, $R^{8a}$, and $R^{8b}$, are each independently selected from the group consisting of hydrogen, hydrocarbyl, substituted hydrocarbyl, halogen, {—}OH, {—}$NH_2$, {—}SH, {—}$SR^{111}$ {—}$OR^{111}$, and {—}$N(R^{111})_2$; provided that any of $R^{6a}$ and $R^{6b}$, $R^{7a}$ and $R^{7b}$, $R^{8a}$ and $R^{8b}$, may together form a moiety selected from the group consisting of {=}O, {=}S, and {=}$NR^{111}$;

$R^9$, $R^{10a}$, $R^{10b}$, $R^{14}$, $R^{15a}$, $R^{15b}$, $R^{16a}$, $R^{16b}$, and $R^{17}$ are independently selected from the group consisting of hydrogen, hydrocarbyl, substituted hydrocarbyl, and {—}$OR^{112}$;

$R^{111}$ is selected from the group consisting of hydrocarbyl, and substituted hydrocarbyl;

$R^{112}$ is selected from the group consisting of {—}OH, hydrocarbyl, and substituted hydrocarbyl;

two or more R groups selected from the group consisting of $R^1$, $R^2$, $R^3$, $R^{6a}$, $R^{6b}$, $R^{7a}$, $R^{7b}$, $R^{8a}$, $R^{8b}$, $R^{10a}$, $R^{10b}$, $R^{15a}$, $R^{15b}$, $R^{16a}$, and $R^{16b}$, may form part of a ring or a ring system selected from the group consisting of carbocyclic rings, heterocyclic rings, aryl rings, heteroaryl rings, and combinations thereof; and carbons attached to R groups selected from the group consisting $R^5$, $R^{6a}$, $R^{6b}$, $R^{7a}$, $R^{7b}$, $R^{8a}$, $R^{8b}$, $R^{10a}$, $R^{10b}$, $R^{14}$, $R^{15a}$, $R^{15b}$, $R^{16a}$, and $R^{16b}$ may optionally form a carbon-carbon double bond with each other or an adjacent carbon.

Other features and iterations of the invention are described in more detail below.

DETAILED DESCRIPTION OF THE INVENTION

The invention provides an efficient synthetic route for the formation of five and six-membered heterocyclic rings in a one-pot process via an intermolecular reaction using an alcohol and a proton donor. A further advantageous aspect of the process is that an enol ether is also formed on the carbon atom next to the newly formed five or six-membered heterocyclic ring. While it is envisioned that the synthetic route may be utilized in a variety of processes to produce organic compounds from a wide array of starting materials, in an exemplary iteration of the invention the process is utilized to make five and six-membered heterocyclic rings in alkaloids. The alkaloids produced are generally intermediate compounds that may be utilized in additional processes to produce a variety of biologically active (+)-opiates, such as (+)-oxycodone, (+)-oxymorphone, (+)-naltrexone, (+)-naloxone, and (+)-nalbuphine.

(I) Synthesis of Compounds Comprising Formula (II)

The process of the invention provides a one-pot preparation of an alkaloid compound comprising Formula (II). In particular, the invention encompasses a process for the formation of a five or six membered ring that comprises group A as a ring member. Compounds comprising Formula (II) correspond to the following structure:

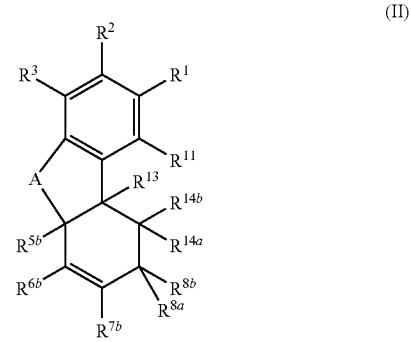

(II)

wherein:

A is a member of a five-membered or a six-membered heterocyclic ring;

$R^1$, $R^2$, $R^3$, and $R^{11}$ are each independently selected from the group consisting of hydrogen, hydrocarbyl, substituted hydrocarbyl, halogen, {—}OH, {—}$NH_2$, {—}SH, {—}$SR^{111}$, {—}$OR^{111}$, and {—}$N(R^{111})_2$;

$R^{5b}$, $R^{6b}$, $R^{7b}$, $R^{8a}$, $R^{8b}$, $R^{13}$, $R^{14a}$, and $R^{14b}$ are each independently selected from the group consisting of hydrogen, hydrocarbyl, substituted hydrocarbyl, halogen, {—}OH, {—}$NH_2$, {—}SH, {—}$SR^{111}$, {—}$OR^{111}$, and {—}$N(R^{111})_2$; provided that any of $R^{8a}$ and $R^{8b}$, $R^{14a}$ and $R^{14b}$, may together form a moiety selected from the group consisting of $\{=\}O$, $\{=\}S$, and $\{=\}NR^{111}$;

$R^{111}$ is selected from the group consisting of hydrocarbyl, and substituted hydrocarbyl; and $R^{112}$ is selected from the group consisting of $\{-\}OH$, hydrocarbyl, and substituted hydrocarbyl.

In one iteration of this embodiment, A is selected from the group consisting of $\{-\}O\{-\}$, $\{-\}S\{-\}$, $\{-\}NH\{-\}$, $\{-\}NR^{112}\{-\}$, $\{-\}N(R^{112})O\{-\}$, $\{-\}P(OH)O\{-\}$, $\{-\}P(R^{112})O\{-\}$, $\{-\}B(OH)O\{-\}$, $\{-\}B(R^{112})O\{-\}$, and $\{-\}Si(R^{112})_2O\{-\}$. Stated another way, the aforementioned groups correspond to the following moieties:

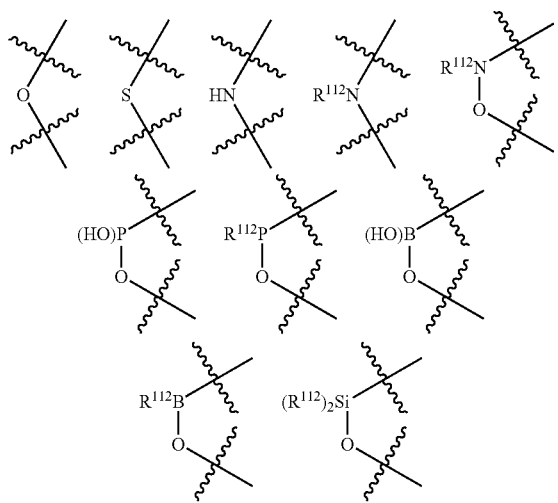

In an exemplary embodiment, the process results in the formation of a compound comprising Formula (IIa);

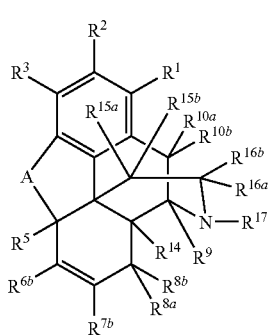

wherein:

A, $R^1$, $R^2$, $R^3$, $R^{6b}$, $R^{7b}$, $R^{8a}$, $R^{8b}$, $R^{111}$ and $R^{112}$ are as described for compounds comprising Formula (II);

$R^5$ is selected from the group consisting of hydrogen, hydrocarbyl, substituted hydrocarbyl, halogen, $\{-\}OH$, $\{-\}NH_2$, $\{-\}SH$, $\{-\}SR^{111}$, $\{-\}OR^{111}$, and $\{-\}N(R^{111})_2$; and $R^9$, $R^{10a}$, $R^{10b}$, $R^{14}$, $R^{15a}$, $R^{15b}$, $R^{16a}$, $R^{16b}$, and $R^{17}$ are independently selected from the group consisting of hydrogen, hydrocarbyl, substituted hydrocarbyl, and $\{-\}OR^{112}$.

The process generally comprises combining a starting material, such as a compound comprising Formula (I), with an alcohol and a proton donor to form a reaction mixture that yields a compound comprising Formula (II). Alternatively, the starting material may comprise a compound comprising Formula (Ia), an alcohol and a proton donor to form a reaction mixture that yields a compound comprising Formula (IIa). Optionally, a scavenger and/or an aprotic solvent may be added to the reaction mixture. The reaction mixture is heated for a sufficient period of time to allow for the formation of the compound having Formula (II) or (IIa). In general, the process results in the formation of both a five or six-membered heterocyclic ring and an enol ether that is formed on the carbon atom next to the newly formed five or six-membered heterocyclic ring to yield compounds comprising Formula (II) or (IIa). The reaction parameters are described in more detail below.

(a) Reaction Mixture

In a step of the process, the starting reagent, a compound comprising Formula (I), is combined with a proton donor and an alcohol to form a reaction mixture that results in the formation of the compound comprising Formula (II). Compounds of Formula (I) correspond to the following structure:

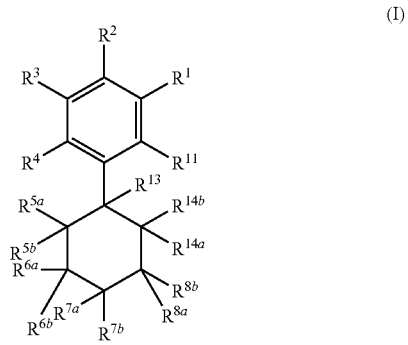

wherein:

$R^1$, $R^2$, $R^3$, and $R^{11}$ are each independently selected from the group consisting of hydrogen, hydrocarbyl, substituted hydrocarbyl, halogen, $\{-\}OH$, $\{-\}NH_2$, $\{-\}SH$, $\{-\}SR^{111}$, $\{-\}OR^{111}$, and $\{-\}N(R^{111})_2$;

$R^4$ is selected from the group consisting of $\{-\}OH$, $\{-\}SH$, $\{-\}NH_2$, $\{-\}NHR^{112}$, $\{-\}N(OH)R^{112}$, $\{-\}P(OH)_2$, $\{-\}P(OH)R^{112}$, $\{-\}B(OH)_2$, $\{-\}B(OH)R^{112}$, and $\{-\}Si(OH)(R^{112})_2$;

$R^{5a}$, $R^{5b}$, $R^{6a}$, $R^{6b}$, $R^{7a}$, $R^{7b}$, $R^{8a}$, $R^{8b}$, $R^{13}$, $R^{14a}$, and $R^{14b}$ are each independently selected from the group consisting of hydrogen, hydrocarbyl, substituted hydrocarbyl, halogen, $\{-\}OH$, $\{-\}NH_2$, $\{-\}SH$, $\{-\}SR^{111}$, $\{-\}OR^{111}$, and $\{-\}N(R^{111})_2$; provided that any of $R^{5a}$ and $R^{5b}$, $R^{6a}$ and $R^{6b}$, $R^{7a}$ and $R^{7b}$, $R^{8a}$ and $R^{8b}$, $R^{14a}$ and $R^{14b}$, may together form a moiety selected from the group consisting of $\{=\}O$, $\{=\}S$, and $\{=\}NR^{111}$;

$R^{111}$ is selected from the group consisting of hydrocarbyl, and substituted hydrocarbyl;

$R^{112}$ is selected from the group consisting of $\{-\}OH$, hydrocarbyl, and substituted hydrocarbyl;

two or more R groups selected from the group consisting of $R^1$, $R^2$, $R^3$, $R^{5a}$, $R^{5b}$, $R^{6a}$, $R^{6b}$, $R^{7a}$, $R^{7b}$, $R^{8a}$, $R^{8b}$, $R^{11}$, $R^{13}$, $R^{14a}$, and $R^{14b}$ may form part of a ring or a ring system selected from the group consisting of carbocyclic rings, heterocyclic rings, aryl rings, heteroaryl rings, and combinations thereof; and two adjacent carbons attached to R groups selected from the group consisting of $R^{5a}$, $R^{5b}$, $R^{6a}$, $R^{6b}$, $R^{7a}$, $R^{7b}$, $R^{8a}$, $R^{8b}$, $R^{13}$, $R^{14a}$, and $R^{14b}$ may optionally form a carbon-carbon double bond.

In one exemplary embodiment, the starting material comprises a compound comprising Formula (Ia), an alcohol, and a proton donor to yield a compound comprising Formula (IIa). Compounds comprising Formula (Ia) correspond to the following structure:

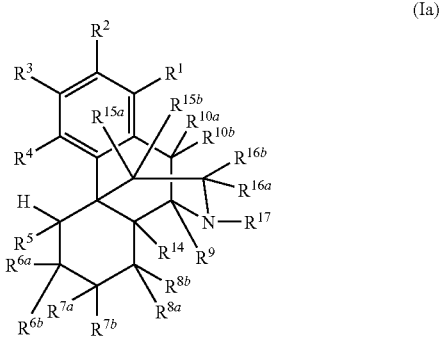

(Ia)

wherein:

$R^1, R^2, R^3, R^4, R^{6a}, R^{6b}, R^{7a}, R^{7b}, R^{8a}, R^{8b}, R^{111}$, and $R^{112}$ are as described for compounds corresponding to Formula (I);

$R^5$ is selected from the group consisting of hydrogen, hydrocarbyl, substituted hydrocarbyl, halogen, {—}OH, {—}NH$_2$, {—}SH, {—}SR$^{111}$, {—}OR$^{111}$, and {—}N(R$^{111}$)$_2$;

$R^9$, $R^{10a}$, $R^{10b}$, $R^{14}$, $R^{15a}$, $R^{15b}$, $R^{16a}$, $R^{16b}$, and $R^{17}$ are independently selected from the group consisting of hydrogen, hydrocarbyl, substituted hydrocarbyl, and {—}OR$^{112}$;

two or more R groups selected from the group consisting of $R^1, R^2, R^3, R^{6a}, R^{6b}, R^{7a}, R^{7b}, R^{8a}, R^{8b}, R^{10a}, R^{10b}, R^{15a}, R^{15b}, R^{16a}$, and $R^{16b}$ may form part of a ring or a ring system selected from the group consisting of carbocyclic rings, heterocyclic rings, aryl rings, heteroaryl rings, and combinations thereof; and carbons attached to R groups selected from the group consisting of $R^5, R^{6a}, R^{6b}, R^{7a}, R^{7b}, R^{8a}, R^{8b}, R^{10a}, R^{10b}, R^{14}, R^{15a}, R^{15b}, R^{16a}$, and $R^{16b}$ may optionally form a carbon-carbon double bond with each other or an adjacent carbon.

Exemplary non-limiting iterations for compounds comprising Formula (Ia) are illustrated in the table below.

| Compound Number | Compound |
|---|---|
| A-1 | |
| A-2 | |
| A-3 | |
| A-4 | |
| A-5 | |
| A-6 | |

-continued

| Compound Number | Compound |
|---|---|
| A-7 | |
| A-8 | |
| A-9 | |
| A-10 | |
| A-11 | |
| A-12 | |
| A-13 | |
| A-14 | |
| A-15 | |
| A-16 | |

The reaction mixture encompasses an alcohol. It is envisioned that a variety of alcohols may be utilized without departing from the scope of the invention. In one embodiment, the alcohol comprises an alkoxyl compound comprising from one to twelve carbon atoms. The arrangement of carbon atoms comprising the alcohol may be linear, branched or combinations thereof. Exemplary alcohols include methanol, ethanol, isopropanol, n-propanol, isobutanol, t-butanol, n-butanol, and combinations thereof. In general, the weight/weight ratio of alcohol to compound comprising Formula (I) or (Ia) may range from about 0.1:1 to about 100:1. In a preferred embodiment, the weight/weight ratio of alcohol to compound comprising Formula (I) or (Ia) may range from about 0.5:1 to about 10:1. In a more preferred embodiment, the weight/weight ratio of alcohol to compound comprising Formula (I) or (Ia) may range from about 1:1 to about 3:1.

The reaction mixture also comprises a proton donor. Suitable proton donors generally have a pKA of less than about 0. Non-limiting examples of suitable proton donors include $H_2SO_4$, HCl, HBr, HI, $H_3PO_4$, $CF_3SO_3H$, $MeSO_3H$, p-toluenesulfonic acid, $HClO_3$, $HBrO_4$, $HIO_3$, $HIO_4$, and combinations thereof. In one embodiment, the molar/molar ratio of compounds comprising Formula (I) or (Ia) to proton donor may range from about 1:1 to about 1:20. In another embodiment, the molar/molar ratio of compounds comprising Formula (I) or (Ia) to proton donor may range from about 1:1.5 to about 1:10. In a preferred embodiment, the molar/molar ratio of compounds comprising Formula (I) or (Ia) to proton donor may range from about 1:1.5 to about 1:4.

In an exemplary embodiment, the alcohol and proton donor are typically contacted with the compound comprising Formula (I) or (Ia) in the presence of an aprotic solvent. The aprotic solvent will generally have a higher boiling point than the alcohol. Non-limiting examples of aprotic solvents include ether solvents, acetonitrile, benzene, N,N-dimethylformamide, dimethyl sulfoxide, N,N-dimethylpropionamide, 1,3-dimethyl-3,4,5,6-tetrahydro-2(1H)-pyrimidinone, 1,3-dimethyl-2-imidazolidinone, 1,2-dimethoxyethane, bis(2-methoxyethyl)ether, N,N-dimethylacetamide, N-methylpyrrolidinone, ethyl acetate, ethyl formate, formamide, hexamethylphosphoramide, methyl acetate, N-methylacetamide, N-methylformamide, 1,2-dichloroethane, nitrobenzene, nitromethane, propionitrile, sulfolane, tetramethylurea, tetrahydrofuran, 2-methyl tetrahydrofuran, toluene, trichloromethane, and combinations thereof. In one embodiment, the weigh/weight ratio of aprotic solvent to compound comprising Formula (I) or (Ia) may range from about 1:1 to about 100:1. In another embodiment, the weight/weight ratio of aprotic solvent to compound comprising Formula (I) or (Ia) may range from about 2:1 to about 20:1. In a preferred embodiment, the weight/weight ratio of aprotic solvent to compound comprising Formula (I) or (Ia) may range from about 2:1 to about 8:1.

The reaction mixture may optionally comprise a water scavenger. As used herein, a "water scavenger" encompasses a reagent that can react with water and may or may not release an alcohol at the same time. The choice of water scavenger can and will vary without departing from the scope of the invention. Suitable examples of water scavengers may include $P_2O_5$, $MgSO_4$, molecular sieves, and $R^{15}(OCH_3)_3$, wherein $R^{15}$ is selected from the group consisting of hydrocarbyl and substituted hydrocarbyl. In one embodiment, the molar/molar ratio of compound comprising Formula (I) or (Ia) to water scavenger may range from about 1:0.5 to about 1:3. In another embodiment, the molar/molar ratio of compound comprising Formula (I) or (Ia) to water scavenger may range from about 1:1 to about 1:2. In a preferred embodiment, the molar/molar ratio of compound comprising Formula (I) or (Ia) to water scavenger may range from about 1:1.1 to about 1:1.3.

(b) Reaction Conditions, Formation of Intermediate Compounds, and Compounds Comprising Formula (II) or (IIa)

In general, the reaction may be conducted at a temperature that ranges from about 20° C. to about 120° C. In a preferred embodiment, the temperature of the reaction may range from about 60° C. to about 100° C. The reaction is preferably performed under ambient pressure, and preferably in an inert atmosphere (e.g., nitrogen or argon).

It will be appreciated by a skilled artisan, that as the reaction proceeds several intermediate compounds can and will be formed. Typically, as the reaction progresses a substantial portion of compounds comprising Formula (I) or (Ia) are first converted to a mixture of intermediates that comprises ketal derivatives. As the reaction further proceeds, a substantial portion of the ketal derivatives is converted to enol ether derivatives. And, as the reaction is completed the ketal derivatives are converted to compounds comprising Formula (II) or (IIa). At each step of the reaction, however, the reaction mixture will typically comprise a mixture intermediate compounds (e.g., ketal derivatives and/or enol ether derivatives) and compounds comprising Formula (I), (Ia), (II), or (IIa).

In particular, the reaction mixture may first be heated to a temperature that ranges from about 20° C. to about 120° C., or more preferably from about 40° C. to about 80° C., and allowed to proceed for a sufficient period of time until a substantial portion of compounds having Formula (I) or (Ia) are converted to a mixture of intermediates comprising ketal derivatives. The ketal derivatives may comprise a moiety or ring structure selected from the group of compounds comprising any of Formulas (III), (IIIa), (IIIb), (IIIc), and (IIId) corresponding to the following structures:

(III)

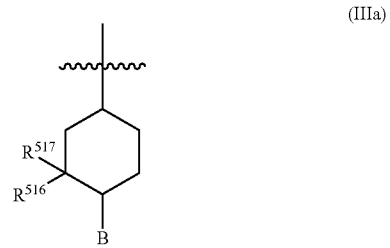

(IIIa)

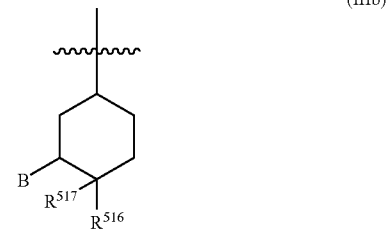

(IIIb)

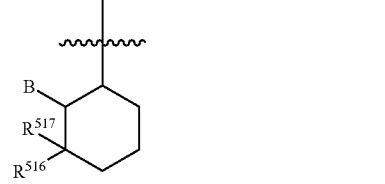

(IIIc)

-continued

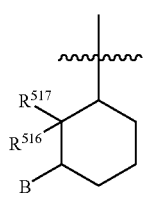
(IIId)

wherein:
B is selected from the group consisting of halogen, {—}OH, {—}OR$^{20}$, {—}SH, and {—}SR$^{20}$;
R$^{20}$ is selected from the group consisting of hydrocarbyl and substituted hydrocarbyl; and
R$^{516}$ and R$^{517}$ are independently selected from the group consisting of {—}OH, {—}OR$^{20}$, {—}SH, and {—}SR$^{20}$.

In another embodiment, the ketal derivatives may comprise a moiety or ring structure selected from the group of compounds comprising any of Formulas (IV), (IVa), (IVb), (IVc), and (IVd) corresponding to the following structures:

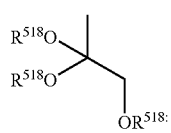
(IV)

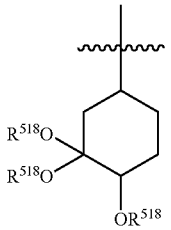
(IVa)

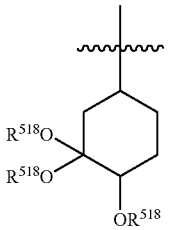
(IVb)

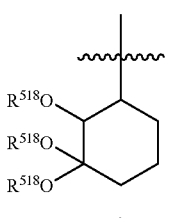
(IVc)

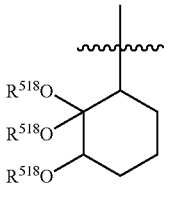
(IVd)

wherein:
R$^{518}$ is selected from the group consisting of hydrocarbyl and substituted hydrocarbyl.

The reaction mixture is then maintained at a temperature that ranges from about 60° C. to about 120° C. and allowed to proceed for a sufficient period of time until a substantial portion of the mixture of intermediates comprising ketal derivatives is converted to a mixture of intermediates comprising enol ether derivatives. The enol ether derivatives may comprise a moiety or ring structure selected from the group of compounds comprising any of Formulas (V), (Va), (Vb), (Vc), (Vd), (VI), (VIa), (VIb), (VIc), and (VId) corresponding to the following structures:

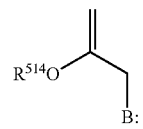
(V)

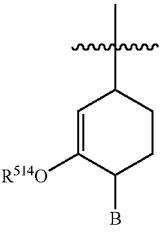
(Va)

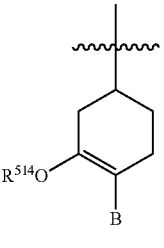
(Vb)

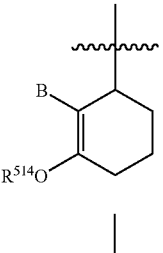
(Vc)

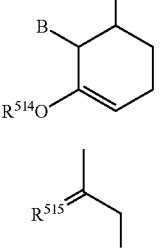
(Vd)

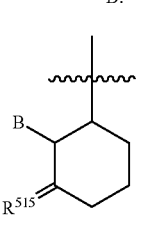
(VI)

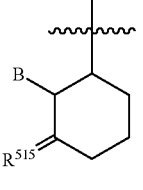
(VIa)

(VIb)

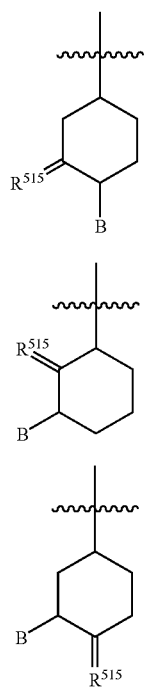

(VIc)

(VId)

wherein:

$R^{21}$ is selected from the group consisting of {—}OH, hydrocarbyl, and substituted hydrocarbyl;

$R^{514}$ is selected from the group consisting of hydrocarbyl and substituted hydrocarbyl; and $R^{515}$ is selected from the group consisting of O, S, and $NR^{21}$.

In another embodiment, the enol ether derivatives may comprise a moiety or ring structure selected from the group of compounds comprising any of Formulas (VII), (VIIa), (VIIb), (VIIc), and (VIId) corresponding to the following structures:

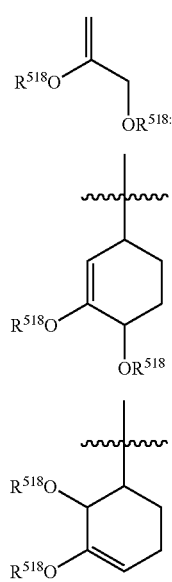

(VII)

(VIIa)

(VIIb)

(VIIc)

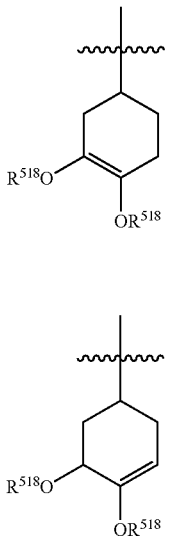

(VIId)

wherein:

$R^{518}$ is selected from the group consisting of hydrocarbyl and substituted hydrocarbyl.

Optionally, the alcohol may be removed from the reaction mixture after the formation of reaction intermediates comprising enol ether compound. In an exemplary embodiment, the alcohol may be removed by distillation.

Typically, the reaction is allowed to proceed for a sufficient period of time until the reaction is complete, as determined by chromatography (e.g., HPLC). In this context, a "completed reaction" generally means that the reaction mixture contains a significantly diminished amount of compounds comprising either Formula (I) or (Ia) and a significantly increased amount of compounds comprising Formula (II) or (IIa) compared to the amounts of each present at the beginning of the reaction. Typically, the amount of compounds comprising Formula (I) or (Ia) remaining in the reaction mixture may be less than about 5%.

The yield of the compound comprising Formula (II) or (IIa) may vary. Typically, the yield of the compound may range from about 50% to about 90%. In one embodiment, the yield of the compound may range from about 50% to about 60%. In another embodiment, the yield of the compound may range from about 60% to about 70%. In a further embodiment, the yield of the compound may range from about 70% to about 80%. In still another embodiment, the yield of the compound may range from about 80% to about 90%.

(II) Synthesis of Compounds Comprising Formula (VIII) or (VIIIa)

Any of the compounds comprising Formulas (II) or (IIa) may be subjected to hydrolysis to form a compound comprising Formula (VIII) or (VIIIa). The hydrolysis may be achieved by methods commonly known in the art, such as by contacting the compounds comprising Formulas (II) or (IIa) with water or a proton donor under suitable reaction conditions. In this regard, hydrolysis of the compound comprising Formula (II) yields a compound comprising Formula (VIII), and hydrolysis of the compound comprising (IIa) yields a compound comprising Formula (VIIIa). Compounds comprising Formula (VIII) correspond to the following structure:

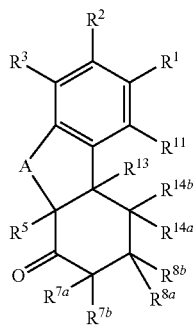

(VIII)

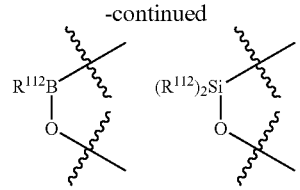

In another embodiment, compounds comprising Formula (VIIIa) correspond to the following structure:

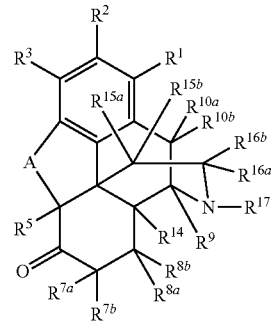

(VIIIa)

wherein:

A is a member of a five-membered or a six-membered heterocyclic ring;

$R^1$, $R^2$, $R^3$, and $R^{11}$ are each independently selected from the group consisting of hydrogen, hydrocarbyl, substituted hydrocarbyl, halogen, {—}OH, {—}NH$_2$, {—}SH, {—}SR$^{111}$, {—}OR$^{111}$, and {—}N(R$^{111}$)$_2$;

$R^5$, $R^{7a}$, $R^{7b}$, $R^{8a}$, $R^{8b}$, $R^{13}$, $R^{14a}$, and $R^{14b}$ are each independently selected from the group consisting of hydrogen, hydrocarbyl, substituted hydrocarbyl, halogen, {—}OH, {—}NH$_2$, {—}SH, {—}SR$^{111}$, {—}OR$^{111}$, and {—}N(R$^{111}$)$_2$; provided that any $R^{7a}$ and $R^{7b}$, $R^{8a}$ and $R^{8b}$, $R^{14a}$ and $R^{14b}$, may together form a moiety selected from the group consisting of {=}O, {=}S, and {=}NR$^{111}$;

$R^{111}$ is selected from the group consisting of hydrocarbyl, and substituted hydrocarbyl;

$R^{112}$ is selected from the group consisting of {—}OH, hydrocarbyl, and substituted hydrocarbyl;

two or more R groups selected from the group consisting of $R^1$, $R^2$, $R^3$, $R^{7a}$, $R^{7b}$, $R^{8a}$, $R^{8b}$, $R^{13}$, $R^{14a}$, and $R^{14b}$ may form part of a ring or a ring system selected from the group consisting of carbocyclic rings, heterocyclic rings, aryl rings, heteroaryl rings, and combinations thereof; and two adjacent carbons attached to R groups selected from the group consisting of $R^5$, $R^{7a}$, $R^{7b}$, $R^{8a}$, $R^{8b}$, $R^{13}$, $R^{14a}$, and $R^{14b}$ may optionally form a carbon-carbon double bond.

In an iteration of this embodiment, A is selected from the group consisting of {—}O{—}, {—}S{—}, {—}NH{—}, {—}NR$^{112}${—}, {—}N(R$^{112}$)O{—}, {—}P(OH)O{—}, {—}P(R$^{112}$)O{—}, {—}B(OH)O{—}, {—}B(R$^{112}$)O{—}, and {—}Si(R$^{112}$)$_2$O{—}. Stated another way, the aforementioned groups correspond to the following moieties:

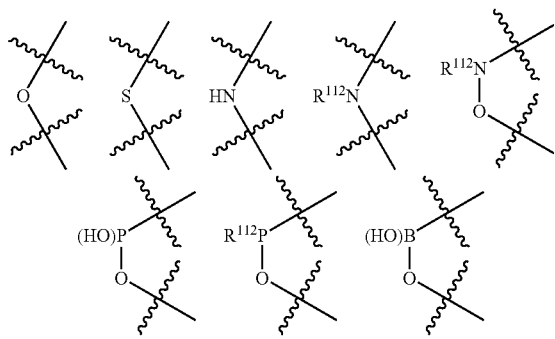

wherein:

A, $R^1$, $R^2$, $R^3$, $R^5$, $R^{7a}$, $R^{7b}$, $R^{8a}$, $R^{8b}$, $R^{111}$, and $R^{112}$ are as described for compounds comprising Formula (VIII);

$R^9$, $R^{10a}$, $R^{10b}$, $R^{14}$, $R^{15a}$, $R^{15b}$, $R^{16a}$, $R^{16b}$, and $R^{17}$ are independently selected from the group consisting of hydrogen, hydrocarbyl, substituted hydrocarbyl, and {—}OR$^{112}$;

two or more R groups selected from the group consisting of $R^1$, $R^2$, $R^3$, $R^{7a}$, $R^{7b}$, $R^{8a}$, $R^{8b}$, $R^{10a}$, $R^{10b}$, $R^{15a}$, $R^{15b}$, $R^{16a}$, and $R^{16b}$, may form part of a ring or a ring system selected from the group consisting of carbocyclic rings, heterocyclic rings, aryl rings, heteroaryl rings, and combinations thereof; and carbons attached to R groups selected from the group consisting of $R^{1a}$, $R^{7b}$, $R^{8a}$, $R^{8b}$, $R^{10a}$, $R^{10b}$, $R^{14}$, $R^{15a}$, $R^{15b}$, $R^{16a}$, and $R^{16b}$, may optionally form a carbon-carbon double bond with each other or an adjacent carbon.

In one exemplary embodiment of the invention, the process comprises use of a compound of Formula (Ia) that comprises Formula (Ia-1) as a starting material that is converted to a compound of Formula (IIa) that comprises Formula (IIa-1). The compound of Formula (IIa-1) may be subjected to hydrolysis to form a compound of Formula (VIIIa) that comprises Formula (VIIIa-1). Each of Formulas (Ia-1), (IIa-1), and (VIIIa-1) comprise the following structures:

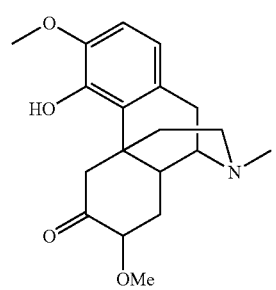

(Ia-1)

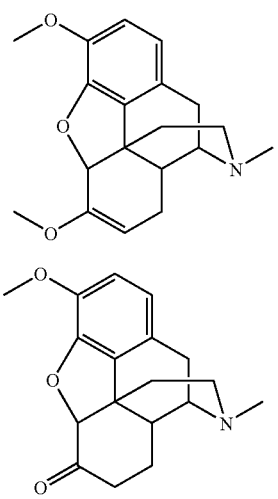

(IIa-1)

(VIIIa-1)

In another exemplary embodiment of the invention, the process comprises use of a compound of Formula (Ia) that comprises Formula (Ia-2) as a starting material that is converted to a compound of Formula (IIa) that comprises Formula (IIa-2). The compound of Formula (IIa-2) may be subjected to hydrolysis to form a compound of Formula (VIIIa) that comprises Formula (VIIIa-2). Each of Formulas (Ia-2), (IIa-2), and (VIIIa-2) comprise the following structures:

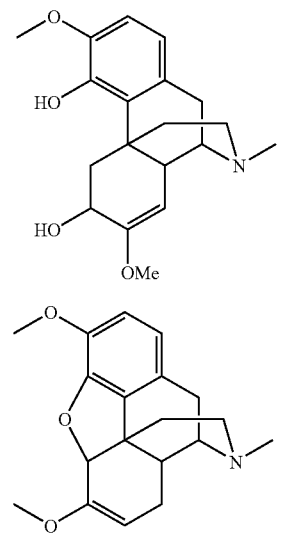

(Ia-2)

(IIa-2)

(VIIIa-2)

In an additional exemplary embodiment of the invention, the process comprises use of a compound of Formula (Ia) that comprises Formula (Ia-3) as a starting material that is converted to a compound of Formula (IIa) that comprises Formula (IIa-3). The compound of Formula (IIa-3) may be subjected to hydrolysis to form a compound of Formula (VIIIa) that comprises Formula (VIIIa-3). Each of Formulas (Ia-3), (IIa-3), and (VIIIa-3) comprise the following structures;

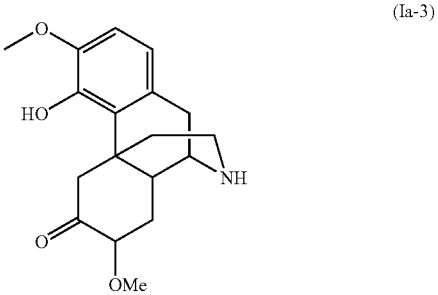

(Ia-3)

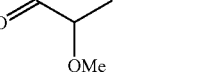

(IIa-3)

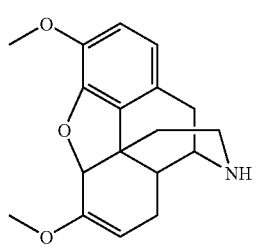

(VIIIa-3)

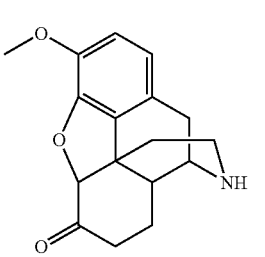

In a further exemplary embodiment of the invention, the process comprises use of a compound of Formula (Ia) that comprises Formula (Ia-4) as a starting material that is converted to a compound of Formula (IIa) that comprises Formula (IIa-4). The compound of Formula (IIa-4) may be subjected to hydrolysis to form a compound of Formula (VIIIa) that comprises Formula (VIIIa-4). Each of Formulas (Ia-4), (IIa-4), and (VIIIa-4) comprise the following structures:

(Ia-4)

-continued

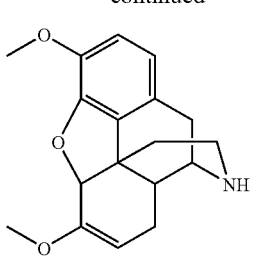

(IIa-4)

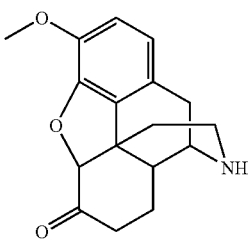

(VIIIa-4)

Other exemplary iterations of the process and compounds formed from the process are described in more detail in the Examples.

The compounds comprising any of Formulas (I), (Ia), (II), (IIa), (VIII), (VIIIa) or any of the intermediates detailed herein may have a (−) or (+) stereochemistry configuration with respect to the rotation of polarized light. More specifically, each chiral center may have an R or an S configuration. The compounds formed by the processes of the invention comprise morphinans. For purposes of illustration, the ring atoms of a morphinan compound are numbered as diagrammed below.

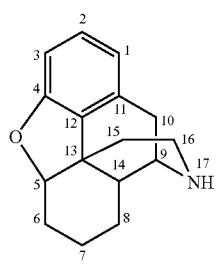

Some compounds described herein, such as compounds comprising Formula (I) or (Ia), may have three chiral centers, namely carbons 13, 14, and 9 (C13, C14, and C9). For these compounds, the stereochemistry for C13, C14, and C9 may be selected from the group consisting of RRR, RSR, RRS, RSS, SRR, SSR, SRS, and SSS. In this iteration, C15 and C16 carbons are both either on the alpha face of the molecule or the beta face of the molecule.

Alternatively, other compounds described herein, such as compounds comprising Formula (II), (IIa), (VIII) or (VIIIa), may have four chiral centers, namely C-5, C-13, C-14, and C-9. For these compounds, the stereochemistry for C-5, C-13, C-14, and C-9 may be selected from the group consisting of RRRR, RRSR, RRRS, RRSS, RSRR, RSSR, RSRS, RSSS, SRRR, SRSR, SRRS, SRSS, SSRR, SSSR, SSRS, and SSSS. In this iteration, C15 and C16 carbons are both either on the alpha face of the molecule or the beta face of the molecule.

The invention also encompasses use of pharmaceutically acceptable salts of any of the compounds described herein. Pharmaceutically acceptable cations include metallic ions and organic ions. More preferred metallic ions include, but are not limited to appropriate alkali metal salts, alkaline earth metal salts and other physiologically acceptable metal ions. Exemplary ions include aluminum, calcium, lithium, magnesium, potassium, sodium and zinc in their usual valences. Preferred organic ions include protonated tertiary amines and quaternary ammonium cations, including in part, trimethylamine, diethylamine, N,N'-dibenzylethylenediamine, chloroprocaine, choline, diethanolamine, ethylenediamine, meglumine (N methylglucamine) and procaine. Exemplary pharmaceutically acceptable acids include without limitation hydrochloric acid, hydrobromic acid, phosphoric acid, sulfuric acid, methanesulfonic acid, acetic acid, formic acid, tartaric acid, maleic acid, malic acid, citric acid, isocitric acid, succinic acid, lactic acid, gluconic acid, glucuronic acid, pyruvic acid, oxalacetic acid, fumaric acid, propionic acid, aspartic acid, glutamic acid, benzoic acid, and the like.

DEFINITIONS

The compounds described herein may have asymmetric centers. Compounds of the present invention containing an asymmetrically substituted atom may be isolated in optically active or racemic form. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated. All processes used to prepare compounds of the present invention and intermediates made therein are considered to be part of the present invention.

The term "acyl," as used herein alone or as part of another group, denotes the moiety formed by removal of the hydroxy group from the group COOH of an organic carboxylic acid, e.g., RC(O)—, wherein R is $R^1$, $R^1O$—, $R^1R^2N$—, or $R^1S$—, $R^1$ is hydrocarbyl, heterosubstituted hydrocarbyl, or heterocyclo, and $R^2$ is hydrogen, hydrocarbyl or substituted hydrocarbyl.

The term "acyloxy," as used herein alone or as part of another group, denotes an acyl group as described above bonded through an oxygen linkage (O), e.g., RC(O)O— wherein R is as defined in connection with the term "acyl."

The term "alkyl" as used herein describes groups which are preferably lower alkyl containing from one to eight carbon atoms in the principal chain and up to 20 carbon atoms. They may be straight or branched chain or cyclic and include methyl, ethyl, propyl, isopropyl, butyl, hexyl and the like.

The term "alkenyl" as used herein describes groups which are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

The term "alkynyl" as used herein describes groups which are preferably lower alkynyl containing from two to eight carbon atoms in the principal chain and up to 20 carbon atoms. They may be straight or branched chain and include ethynyl, propynyl, butynyl, isobutynyl, hexynyl, and the like.

The term "aromatic" as used herein alone or as part of another group denotes optionally substituted homo- or heterocyclic aromatic groups. These aromatic groups are preferably monocyclic, bicyclic, or tricyclic groups containing from 6 to 14 atoms in the ring portion. The term "aromatic" encompasses the "aryl" and "heteroaryl" groups defined below.

The term "aryl" or "Ar" as used herein alone or as part of another group denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl and substituted phenyl are the more preferred aryl.

The terms "halogen" or "halo" as used herein alone or as part of another group refer to chlorine, bromine, fluorine, and iodine.

The term "heteroatom" shall mean atoms other than carbon and hydrogen.

The terms "heterocyclo" or "heterocyclic" as used herein alone or as part of another group denote optionally substituted, fully saturated or unsaturated, monocyclic or bicyclic, aromatic or non-aromatic groups having at least one heteroatom in at least one ring, and preferably 5 or 6 atoms in each ring. The heterocyclo group preferably has 1 or 2 oxygen atoms and/or 1 to 4 nitrogen atoms in the ring, and is bonded to the remainder of the molecule through a carbon or heteroatom. Exemplary heterocyclo groups include heteroaromatics as described below. Exemplary substituents include one or more of the following groups: hydrocarbyl, substituted hydrocarbyl, hydroxy, protected hydroxy, acyl, acyloxy, alkoxy, alkenoxy, alkynoxy, aryloxy, halogen, amido, amino, cyano, ketals, acetals, esters and ethers.

The term "heteroaryl" as used herein alone or as part of another group denote optionally substituted aromatic groups having at least one heteroatom in at least one ring, and preferably 5 or 6 atoms in each ring. The heteroaryl group preferably has 1 or 2 oxygen atoms and/or 1 to 4 nitrogen atoms in the ring, and is bonded to the remainder of the molecule through a carbon. Exemplary heteroaryls include furyl, benzofuryl, oxazolyl, isoxazolyl, oxadiazolyl, benzoxazolyl, benzoxadiazolyl, pyrrolyl, pyrazolyl, imidazolyl, triazolyl, tetrazolyl, pyridyl, pyrimidyl, pyrazinyl, pyridazinyl, indolyl, isoindolyl, indolizinyl, benzimidazolyl, indazolyl, benzotriazolyl, tetrazolopyridazinyl, carbazolyl, purinyl, quinolinyl, isoquinolinyl, imidazopyridyl and the like. Exemplary substituents include one or more of the following groups: hydrocarbyl, substituted hydrocarbyl, hydroxy, protected hydroxy, acyl, acyloxy, alkoxy, alkenoxy, alkynoxy, aryloxy, halogen, amido, amino, cyano, ketals, acetals, esters and ethers.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The "substituted hydrocarbyl" moieties described herein are hydrocarbyl moieties which are substituted with at least one atom other than carbon, including moieties in which a carbon chain atom is substituted with a hetero atom such as nitrogen, oxygen, silicon, phosphorous, boron, sulfur, or a halogen atom. These substituents include halogen, heterocyclo, alkoxy, alkenoxy, aryloxy, hydroxy, protected hydroxy, acyl, acyloxy, nitro, amino, amido, nitro, cyano, ketals, acetals, esters and ethers.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

Having described the invention in detail, it will be apparent that modifications and variations are possible without departing from the scope of the invention defined in the appended claims.

EXAMPLES

The following examples illustrate various aspects of the present invention.

Example 1

Synthesis of (+)-Dihydrothebaine from Dihydrosinomenine in a One Pot Reaction

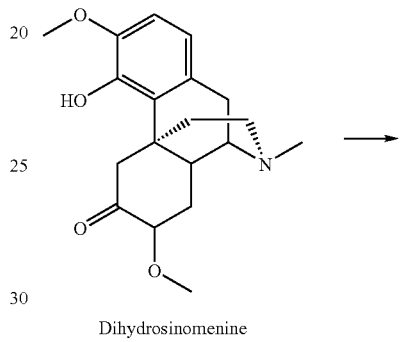

Dihydrosinomenine

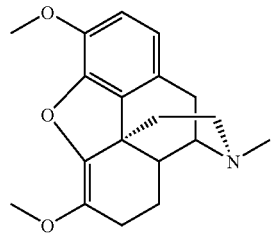

(+)-Dihydrothebaine

To demonstrate the feasibility of forming (+)-dihydrothebaine from dihydrosinomenine according to the scheme illustrated above, the following experiment was conducted.

First, 165 grams of 7,8-dihydrosinomenine (98% by weight) was placed into a 2 L three-neck flask. 82.5 mL of methanol (MeOH), 1320 mL of acetonitrile (ACN), and 109.5 mL of trimethoxymethane ($CH(OMe)_3$) were then added to the three-neck flask and the agitator was turned on. Nitrogen was flashed into the flask for ten minutes, and the reactor was kept under nitrogen for the remainder of the reaction.

Then 97.3 mL of methanesulfonic acid ($MeSO_3H$) was introduced into the three-neck flask, and the temperature of the reaction mixture inside the flask was increased to 63° C. and maintained at this temperature (J-Ken temperature control, power level=2 L) for thirty minutes. The temperature of the reaction mixture was then increased to 85° C. and 825 mL of solvent was distilled off of the reaction mixture over a period of 60 minutes.

An additional 413 mL of ACN was added to the three-neck flask, followed by an additional 32.4 mL of MeSO₃H, while maintaining the temperature of the reaction mixture at 85° C. 413 mL more solvent was distilled off of the reaction mixture over the next thirty minutes. The reaction mixture was then cooled to a temperature of 15° C.-30° C.

An additional 413 mL of ACN was added to the three-neck flask, followed by an additional 32.4 mL of MeSO₃H, and then the temperature of the reaction mixture was increased to 88° C. An additional 413 mL more solvent was distilled off of the reaction mixture over the next thirty minutes at 88° C., and then the temperature of the reaction mixture was decreased to 85° C. and maintained at this temperature for an additional two hours. After two hours at 85° C., the temperature of the reaction mixture was increased to 88° C. and an additional 165 mL more solvent was distilled off of the reaction mixture over thirty minutes.

The reaction mixture was then cooled to a temperature of 15° C.-30° C. 413 mL of icy cooled water was added to a 3 L three-neck flask, and then 248 mL of 28% ammonium hydroxide (NH₄OH) was added to the 3 L three-neck flask. The NH₄OH solution was cooled to a temperature of 0° C.-5° C., and agitated at high speed. The 3 L three-neck flask was then flashed with nitrogen for 10 minutes and the reactor was maintained under nitrogen throughout the quenching procedure.

The reaction mixture in the 2 L three-neck flask was combined with the NH₄OH solution in the 3 L three-neck flask, and the temperature of the mixture was kept below 40° C. over a twenty-minute period. An additional 1485 mL of water was slowly added to the 3 L three-neck flask during this period to force out more precipitates. Fast agitation was maintained in the mixture for an additional 30 minutes, and then the agitation was decreased to normal agitation speed.

The mixture was cooled to 0° C.-5° C., maintained at this temperature for one hour, and then filtered. The solid cake on the filter was washed three times with 165 mL of water. The wet cake was then dried under vacuum at a temperature of 65° C. for 18 hours. The resulting dried product was 85.2 grams of (+)-dihydrothebaine.

The results of this experiment demonstrated that (+)-dihydrothebaine could be formed from dihydrosinomenine using the process described above.

Example 2

Synthesis of Dihydrosinomenine from Sinomenine

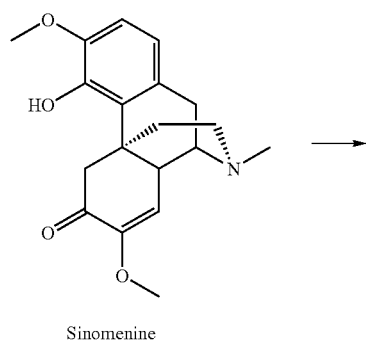

Sinomenine

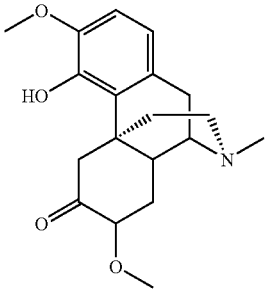

Dihydrosinomenine

To demonstrate the feasibility of forming dihydrosinomenine from sinomenine according to the scheme illustrated above, the following experiment was conducted.

Sinomenine.HCl.xH₂O containing about 80% sinomenine base by weight was placed into a flask. About 1-4 mL of water for each gram of sinomenine.HCl.xH₂O was added to the flask. Agitation of the reaction mixture was then initiated and maintained throughout the rest of the procedure. In addition, nitrogen was introduced into the flask and maintained throughout the rest of the procedure.

One mL of methanol (MeOH) per gram of sinomenine.HCl.xH₂O was added to the reaction mixture in the flask, followed by 0.086 mL of acetic acid (HOAc) per gram of sinomenine.HCl.xH₂O and 0.01-0.05 gram of 5% palladium on carbon catalyst (Pd/C) per gram of sinomenine.HCl.xH₂O. The reactor was then purged with nitrogen a total of four times, and then purged with hydrogen a total of four times. The reaction mixture was then stirred for 10 minutes under an atmosphere of hydrogen at a pressure of 40 psi. The reaction mixture was then cooled to room temperature while maintaining the hydrogen atmosphere. The reactor was again purged with nitrogen a total of four times. After the completion of purging, a sample of the reaction mixture was removed for HPLC analysis.

If the results of HPLC analysis indicated that the reaction was complete the procedure continued to the next phase. Otherwise, if the reaction was determined to be incomplete by HPLC analysis, the hydrogenation procedure was repeated by adding another 0.05 grams of 5% Pd/C per gram of sinomenine.HCl.xH₂O in the reaction mixture, purging the reactor with nitrogen for a total of four times, and then purging the reactor with hydrogen for a total of four times. The reaction mixture was then stirred again for 10 minutes under an atmosphere of hydrogen at a pressure of 40 psi, and cooled to room temperature while maintaining the 40 psi hydrogen atmosphere. The reactor was then purged with nitrogen a total of four times, and an additional sample was taken for HPLC analysis. If the reaction was determined to be incomplete, the hydrogenation procedure was repeated as necessary. Once HPLC analysis indicated that the reaction was complete, the procedure continued to the next phase.

Sodium pyrosulfate (NaSHO₃) in the amount of 0.01 grams per gram of sinomenine.HCl.xH₂O in the reaction mixture was added as an anti-oxidant and color-reducing agent to the reaction mixture. The reaction mixture was heated to a temperature of 50° C. and then filtered. The solid filtrate obtained was then washed using 2% HOAc in water in an amount of at least 4 mL per gram of sinomenine.HCl.xH₂O in the original reaction mixture. The rinsed filtrate solution was then cooled to a temperature of 30° C.-50° C., and flashed with nitrogen. The filtrate solution was then adjusted to a pH of 7-7.5 using ammonium hydroxide (c-NH₄OH) and stirred at a temperature of 30° C.-50° C. for 30 minutes or longer until a precipitate formed, seeding the filtrate solution with dihydrosinomenine crystals as necessary.

The pH of the filtrate solution was adjusted to a pH of 10 using c-NH₄OH and maintained at a temperature of 30° C.-50° C. for 30 minutes, cooled to 0° C.-5° C. for 2 hours, and then filtered. The filtered solids were washed three times with 0.3 mL of water per gram of sinomenine.HCl.xH₂O in the original reaction mixture. The wet solids were dried in a vacuum at 65° C. for 18 hours. Overall, the method described above produced about 0.70-0.75 grams of white, solid dihydrosinomenine for each gram of sinomenine.HCl.xH₂O in the original reaction mixture, corresponding to a yield of about 90%-96%.

The results of this experiment demonstrated that dihydrosinomenine could be formed from sinomenine using the process described above.

Example 3

Formation of Dimethyl Ketal Derivatives of Dihydrosinomenine

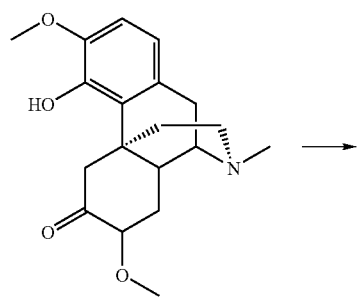

Dihydrosinomenine

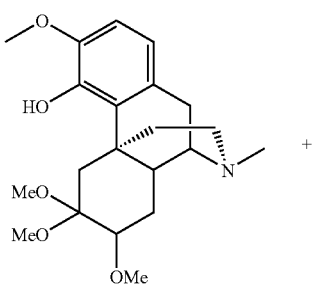

+

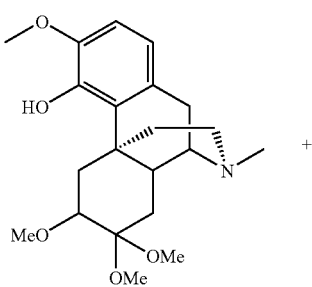

+

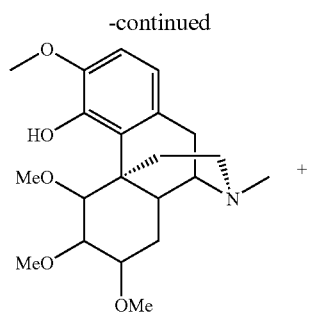

+

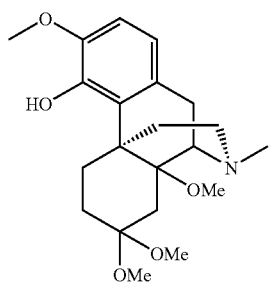

To demonstrate the feasibility of forming dimethyl ketal derivatives of dihydrosinomenine from dihydrosinomenine according to the scheme illustrated above the following experiment was conducted.

First, 165 grams of 7,8-dihydrosinomenine (98% by weight) was added to a 2 L three-neck flask, in addition to 82.5 mL of methanol (MeOH), 1320 mL of acetonitrile (ACN), and 109.5 mL of trimethoxymethane (CH(OMe)₃). The agitation of the reaction mixture was initiated and maintained throughout the procedure. The flask was flashed with nitrogen for 10 minutes, and the remaining procedure was conducted under an atmosphere of nitrogen.

Then 97.3 mL of methanesulfonic acid (MeSO₃H) was added to the reaction mixture, the reaction mixture was heated to of 63° C., and the reaction mixture was maintained at this temperature for thirty minutes, forming a mixture of dimethyl ketal derivatives of dihydrosinomenine.

The results of this experiment demonstrated that ketone derivatives of dihydrosinomenine could be formed from dihydrosinomenine using the process described above.

Example 4

Formation of Enol-ether Derivatives of Dihydrosinomenine

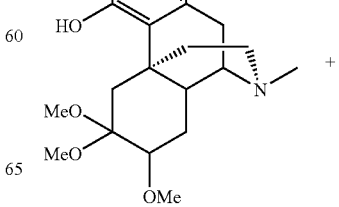

+

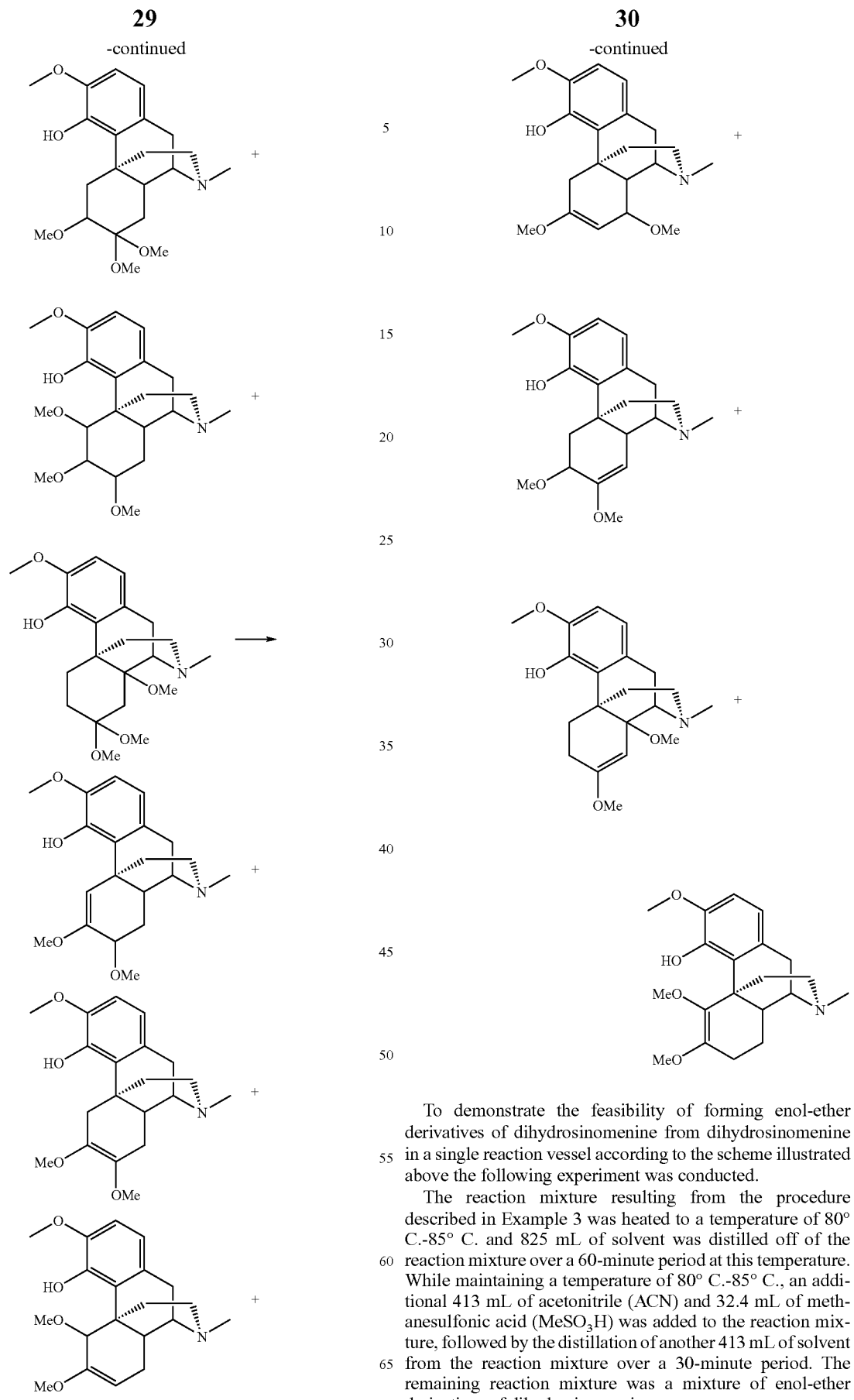

To demonstrate the feasibility of forming enol-ether derivatives of dihydrosinomenine from dihydrosinomenine in a single reaction vessel according to the scheme illustrated above the following experiment was conducted.

The reaction mixture resulting from the procedure described in Example 3 was heated to a temperature of 80° C.-85° C. and 825 mL of solvent was distilled off of the reaction mixture over a 60-minute period at this temperature. While maintaining a temperature of 80° C.-85° C., an additional 413 mL of acetonitrile (ACN) and 32.4 mL of methanesulfonic acid (MeSO$_3$H) was added to the reaction mixture, followed by the distillation of another 413 mL of solvent from the reaction mixture over a 30-minute period. The remaining reaction mixture was a mixture of enol-ether derivatives of dihydrosinomenine.

The results of this experiment demonstrated that enol-ether derivatives of dihydrosinomenine could be formed from dihydrosinomenine using the process described above.

Example 5

Synthesis of (+)-Dihydrothebaine from Enol-ether Derivatives of Dihydrosinomenine

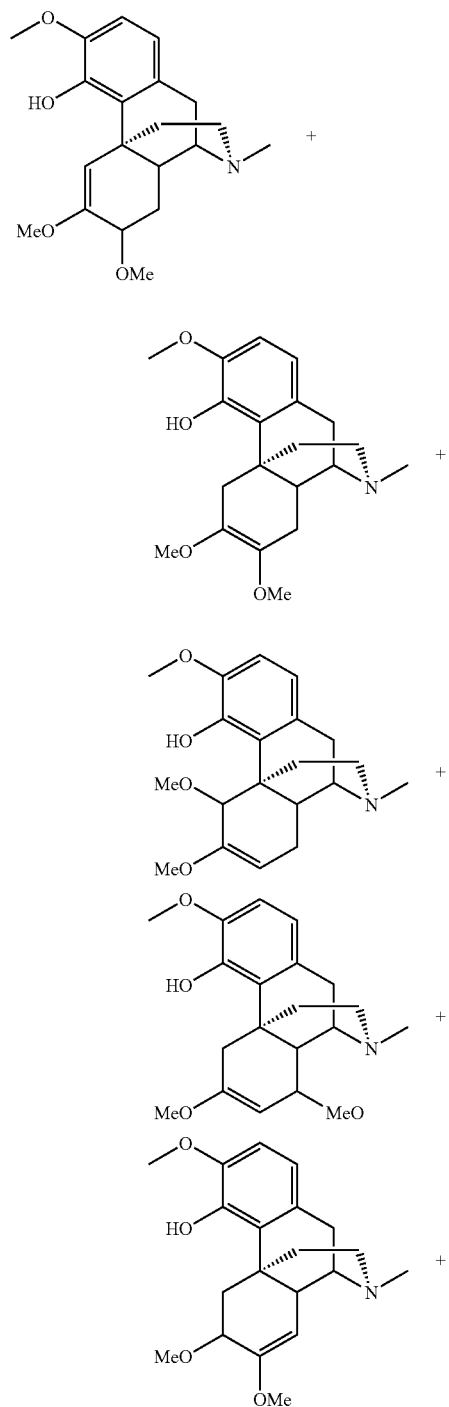

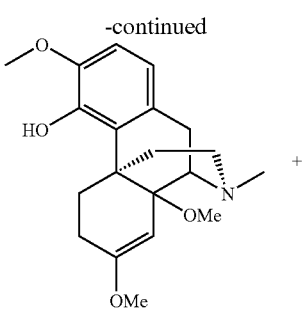

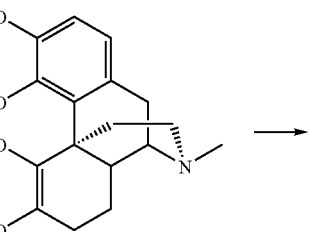

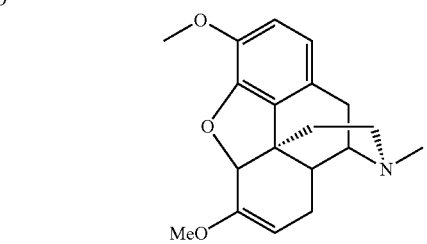

To demonstrate the feasibility of forming (+)-dihydrothebaine from enol-ether derivatives of dihydrosinomenine according to the scheme illustrated above, the following experiment was conducted.

The reaction mixture resulting from the procedure described in Example 4 was heated to a temperature of 85° C.-88° C. with slight reflux for 2 hours. 165 mL of solvent was then distilled off of the reaction mixture at a temperature of 85° C.-88° C. over a thirty-minute period, forming dihydrothebaine.

The results of this experiment demonstrated that (+)-dihydrothebaine could be formed from enol-ether derivatives of dihydrosinomenine using the process described above.

Example 6

Reversion of Unreacted Enol-Ether Derivatives of Dihydrosinomenine to Dimethyl Ketal Derivatives of Dihydrosinomenine and Generating Additional (+)-Dihydrothebaine

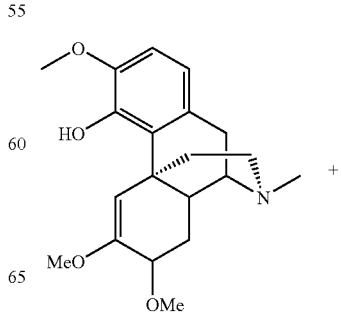

-continued

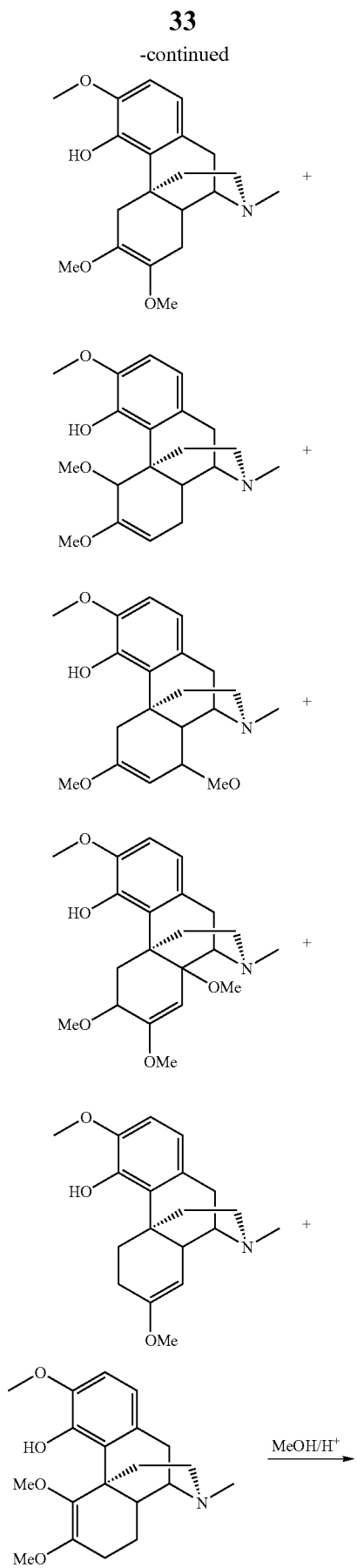

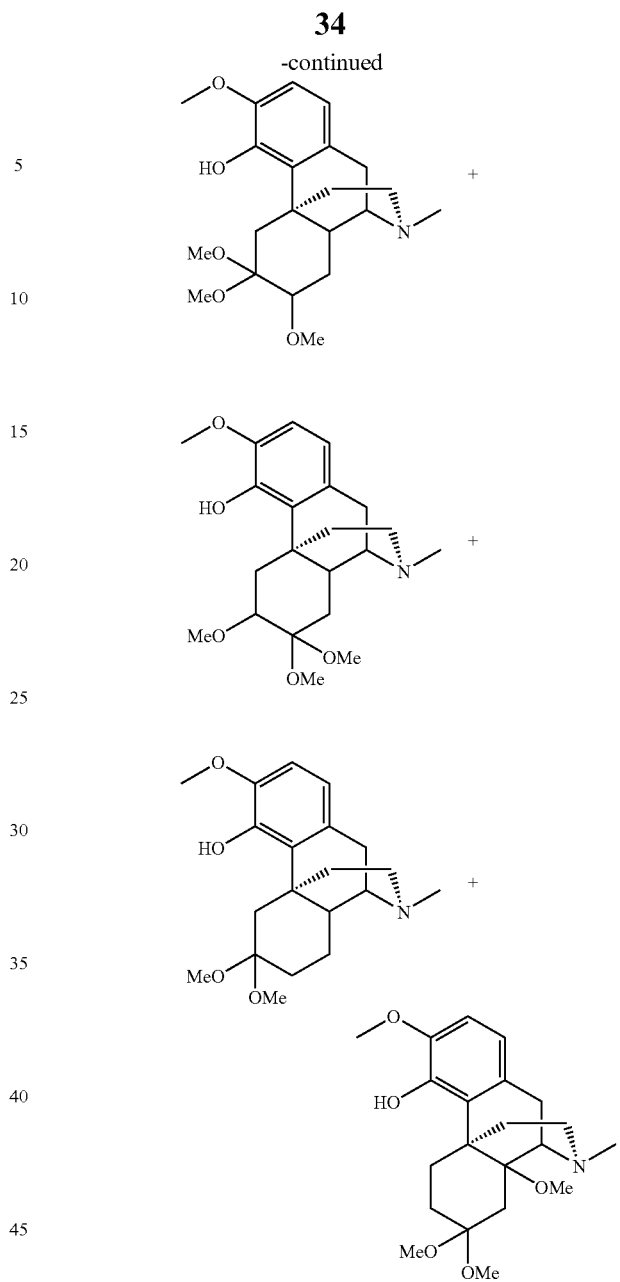

To demonstrate the feasibility of forming additional (+)-dihydrothebaine from the unreacted enol-ether derivatives of dihydrosinomenine according to the scheme illustrated above, the following experiment was conducted. The procedure described in Experiment 5 converted most of the enol-ether derivatives of dihydrosinomenine in the reaction mixture to (+)-dihydrothebaine. However, a small proportion of the enol-ether derivatives of dihydrosinomenine in the reaction mixture were not as reactive and remained unconverted in the reaction mixture after the completion of the procedure described in Example 5. The procedure of this experiment converted a portion of the unreacted enol-ether derivatives of dihydrosinomenine remaining in the reaction mixture back into dimethyl ketal derivatives of dihydrosinomenine, and then repeated the procedures to convert the dimethyl ketal derivatives to enol-ether derivatives of dihydrosinomenine, as described in Experiment 4, then converting the enol-ether derivatives of dihydrosinomenine into (+)-dihydrothebaine, as described in Experiment 5.

The unreacted enol-ether derivatives were converted back into dimethyl ketal derivatives of dihydrosinomenine using the following procedure. 42 mL of methanol (MeOH), 826 mL of acetonitrile (ACN) and 16.2 mL of methanesulfonic acid (MeSO$_3$H) were added to the reaction mixture resulting from the procedure described in Experiment 5, and the reaction mixture was heated to a temperature of 63° C. for 30 minutes. At this point, the most of unreacted enol-ether derivatives were converted back into dimethyl ketal derivatives of dihydrosinomenine.

While maintaining a temperature of 63° C., 816 mL of solvent were distilled off of the reaction mixture over a 30-minute period. An additional 413 mL of ACN was added to the reaction mixture and 413 mL of additional solvent was distilled off of the reaction mixture over a period of 30-60 minutes. Another 413 mL of ACN was added to the reaction mixture, and 248 mL of additional solvent was distilled off of the reaction mixture over the next 30-60 minutes. At this point, the most of dimethyl ketal derivatives of dihydrosinomenine formed in the previous step had been converted to enol-ether derivatives.

The reaction mixture was heated to a temperature of 85° C., and maintained at this temperature with slight reflux for two hours, The temperature of the reaction mixture was then increased to 85° C. and 165 mL of additional solvent was distilled, forming dihydrothebaine. The final reaction mixture resulting from the procedure described above contained an amount of dihydrothebaine in excess of the dihydrothebaine contained in the reaction mixture at the end of the procedure described in Experiment 5.

The results of this experiment demonstrated that additional (+)-dihydrothebaine could be formed from unreacted enol-ether derivatives of dihydrosinomenine remaining in the reaction mixture using the procedure described above.

What is claimed is:

1. A process for the preparation of a compound of Formula (IIa):

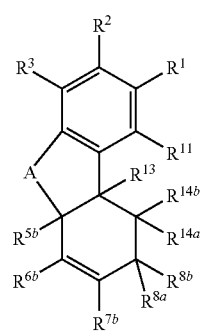
(II)

the process comprising:
(a) contacting a compound of Formula (Ia), with an alcohol and a proton donor having a pKA of less than 0 to form a reaction mixture, wherein a molar ratio of the proton donor to compound of Formula (Ia) is from about 1:1 to about 20:1, and wherein the compound of Formula (Ia) is of the following structure:

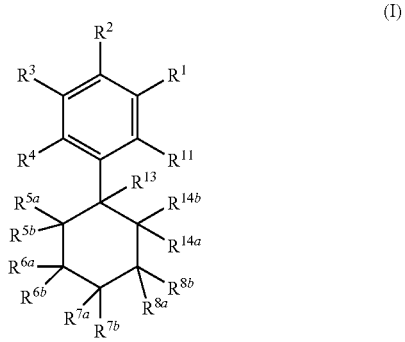
(I)

(b) heating the reaction mixture to form a compound of Formula (IIa), wherein:

A is {—}O{—} and is a member of a five-membered heterocyclic ring;

$R^1$, $R^2$, and $R^3$ are each independently selected from the group consisting of hydrogen, hydrocarbyl, substituted hydrocarbyl, halogen, {—}OH, {—}NH$_2$, {—}SH, {—}SR$^{111}$, {—}OR$^{111}$, and {—}N(R$^{111}$)$_2$;

$R^4$ is selected from the group consisting of {—}OH, {—}SH, {—}NH$_2$, {—}NHR$^{112}$, {—}N(OH)R$^{112}$, {—}P(OH)$_2$, {—]P(OH)R$^{112}$, {—}B(OH)$_2$, {—}B(OH)R$^{112}$, and {—}Si(OH)(R$^{112}$)$_2$;

$R^5$, $R^{6a}$, $R^{6b}$, $R^{7a}$, $R^{7b}$, $R^{8a}$, and $R^{8b}$, are each independently selected from the group consisting of hydrogen, hydrocarbyl, substituted hydrocarbyl, halogen, {—}OH, {—}NH$_2$, {—}SH, {—}SR$^{111}$, {—}OR$^{111}$, and {—}N(R$^{111}$)$_2$; provided that any of $R^{6a}$ and $R^{6b}$, $R^{7a}$ and $R^{7b}$, $R^{8a}$ and $R^{8b}$, may together form a moiety selected from the group consisting of {=}O, {=}S, and {=}NR$^{111}$;

$R^9$, $R^{10a}$, $R^{10b}$, $R^{14}$, $R^{15a}$, $R^{15b}$, $R^{16a}$, $R^{16b}$, and $R^{17}$ are independently selected from the group consisting of hydrogen, hydrocarbyl, substituted hydrocarbyl, and {—}OR$^{112}$;

$R^{111}$ is selected from the group consisting of hydrocarbyl and substituted hydrocarbyl;

$R^{112}$ is selected from the group consisting of {—}H, hydrocarbyl, and substituted hydrocarbyl; and carbons attached to R groups selected from the group consisting of $R^5$, $R^{6a}$, $R^{6b}$, $R^{7a}$, $R^{7b}$, $R^{8a}$, $R^{8b}$, $R^{10a}$, $R^{10b}$, $R^{15a}$, $R^{15b}$, $R^{16a}$, and $R^{16b}$ may optionally form a carbon-carbon double bond with each other or an adjacent carbon.

2. The process of claim 1, wherein the reaction mixture further comprises an aprotic solvent and a water scavenger, the alcohol comprises an alkoxy, and the reaction mixture is heated to a temperature of about 20° C. to about 120° C.

3. The process of claim 1, wherein the reaction mixture is heated to a temperature of about 20° C. to about 120° C. for a period of time sufficient to convert a substantial portion of the compound having Formula (Ia) to a mixture of intermediates comprising ketal derivatives.

4. The process of claim 3, wherein the ketal derivative comprises a moiety or ring structure selected from the group of compounds of any of Formulas (III), (IIIb), (IIIc), and (IIId):

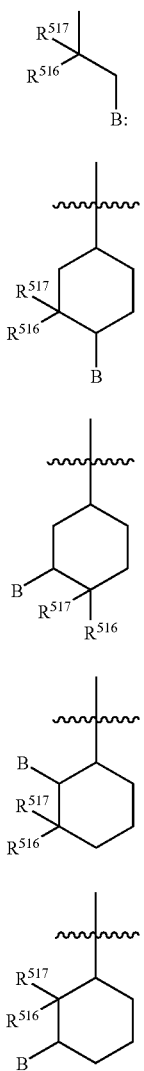

(III)

(IIIa)

(IIIb)

(IIIc)

(IIId)

wherein:

B is selected from the group consisting of halogen, {—}OH, {—}OR$^{20}$, {—}SH, and {—}SR$^{20}$;

R$^{20}$ is selected from the group consisting of hydrocarbyl and substituted hydrocarbyl; and R$^{516}$ and R$^{517}$ are independently selected from the group consisting of {—}OH, {—}OR$^{20}$, {—}SH, and {—}SR$^{20}$.

5. The process of claim 3, wherein the ketal derivative comprises a moiety or ring structure selected from the group of compounds of any of Formulas (IV), (IVa), (IVc), and (IVd):

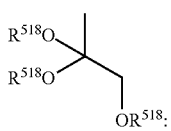

(IV)

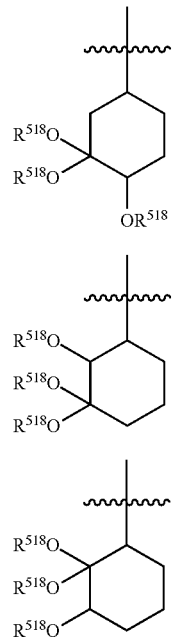

(IVa)

(IVc)

(IVd)

wherein:

R$^{518}$ is selected from the group consisting of hydrocarbyl and substituted hydrocarbyl.

6. The process of claim 3, wherein the reaction mixture is heated to a temperature of about 60° C. to about 120° C. for a period of time sufficient to convert a substantial portion of the mixture of intermediates comprising ketal derivatives to a mixture of intermediates comprising enol ether derivatives.

7. The process of claim 6, wherein the enol ether derivative comprises a moiety or ring structure selected from the group of compounds of any of Formulas (V), (Va), (Vb), (Vc), (Vd), (VI), (VIa), (VIb), (VIc), and (VId):

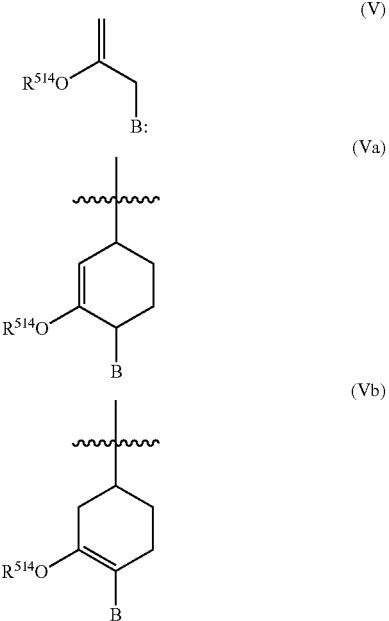

(V)

(Va)

(Vb)

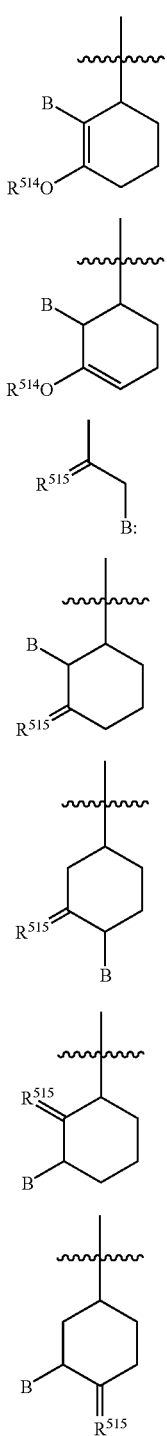

wherein:
- B is selected from the group consisting of halogen, {—}OH, {—}OR20, {—}SH, and {—}SR21;
- $R^{21}$ is selected from the group consisting of {—}H, hydrocarbyl, and substituted hydrocarbyl;
- $R^{514}$ is selected from the group consisting of hydrocarbyl and substituted hydrocarbyl; and
- $R^{515}$ is selected from the group consisting of O, S, and $NR^{21}$.

8. The process of claim 6, wherein the enol ether derivative comprises a moiety or ring structure selected from the group of compounds of any of Formulas (VII), (VIIa), (VIIb), (VIIc), and (VIId);

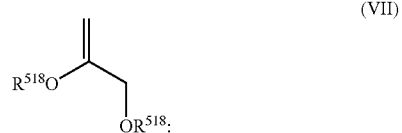

(VII)

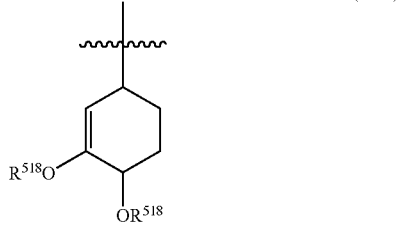

(VIIa)

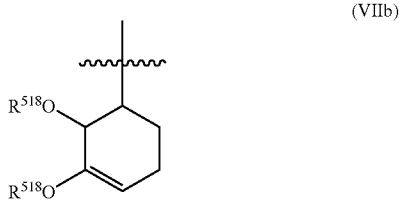

(VIIb)

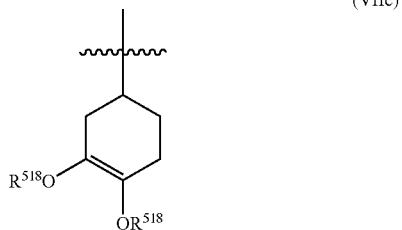

(VIIc)

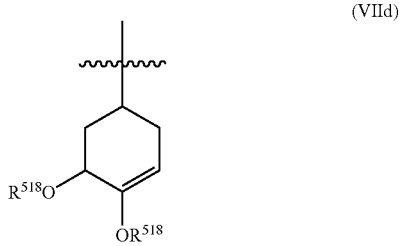

(VIId)

wherein:
$R^{518}$ is selected from the group consisting of hydrocarbyl and substituted hydrocarbyl.

9. The process of claim 6, wherein the alcohol is removed from the reaction mixture after the formation of the mixture of intermediates comprising enol ether derivatives; and the reaction mixture is maintained at a temperature of about 60° C. to about 120° C. for a period of time sufficient to convert a substantial portion of the mixture of intermediates comprising enol ether derivatives to the compound of Formula (IIa).

10. The process of claim 1, further comprising subjecting the compound of Formula (IIa) to hydrolysis to form a compound of Formula (VIIIa):

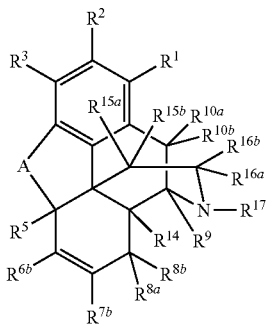

(IIa)

wherein:

A is {—}O{—} and is a member of a five-membered heterocyclic ring;

$R^1$, $R^2$, and $R^3$ are each independently selected from the group consisting of hydrogen, hydrocarbyl, substituted hydrocarbyl, halogen, {—}OH, {—}NH$_2$, {—}SH, {—}SR$^{111}$, {—}OR$^{111}$, and {—}N(R$^{111}$)$_2$;

$R^5$, $R^{7a}$, $R^{7b}$, $R^{8a}$, and $R^{8b}$, are each independently selected from the group consisting of hydrogen, hydrocarbyl, substituted hydrocarbyl, halogen, {—}OH, {—}NH$_2$, {—}SH, {—}SR$^{111}$, and {—}(OR$^{111}$, and {—}N(R$^{111}$)$_2$; provided that any of $R^{7a}$ and $R^{7b}$, $R^{8a}$ and $R^{8b}$, may together form a moiety selected from the group consisting of {=}O, {=}S, and {=}NR$^{111}$;

$R^9$, $R^{10a}$, $R^{10b}$, $R^{14}$, $R^{15a}$, $R^{15b}$, $R^{16a}$, $R^{16b}$, and $R^{17}$ are independently selected from the group consisting of hydrogen, hydrocarbyl, substituted hydrocarbyl, and {—}OR$^{112}$;

$R^{111}$ is selected from the group consisting of hydrocarbyl, and substituted hydrocarbyl;

$R^{112}$ is selected from the group consisting of {—}H, hydrocarbyl, and substituted hydrocarbyl; and carbons attached to R groups selected from the group consisting of $R^{7a}$, $R^{7b}$, $R^{8a}$, $R^{8b}$, $R^{10a}$, $R^{10b}$, $R^{15a}$, $R^{15b}$, $R^{16a}$, and $R^{16b}$ may optionally form a carbon-carbon double bond with each other or an adjacent carbon.

11. The process of claim 1, wherein the optical activity of the compound of Formula (IIa) is selected from the group consisting of (+), (−), and combinations of both; and the configuration of the chiral carbons C-5, C-13, C-14, and C-9 of the compound of comprising Formula (IIa) may be selected from the group consisting of RRRR, RRSR, RRRS, RRSS, RSRR, RSSR, RSRS, RSSS, SRRR, SRSR, SRRS, SRSS, SSRR, SSSR, SSRS, and SSSS; provided, however, that the C-15 and the C-16 carbons are both either on the alpha face of the molecule or the beta face of the molecule.

12. The process of claim 1 wherein the weight/weight ratio of alcohol to compound Formula (Ia) is from about 0.5:1 to about 10:1.

* * * * *